(12) United States Patent
Danos et al.

(10) Patent No.: US 9,468,600 B2
(45) Date of Patent: *Oct. 18, 2016

(54) COMPOSITIONS FOR THE TRANSDERMAL DELIVERY OF PHYSIOLOGICALLY ACTIVE AGENTS

(71) Applicant: Dr. Holmquist Healthcare, LLC, Mandeville, LA (US)

(72) Inventors: C. Scott Danos, Lilburn, GA (US); Bruce A. Cranner, Mandeville, LA (US); Anne-Marie T. Karp, New Orleans, LA (US)

(73) Assignee: DR. HOLMQUIST HEALTHCARE, LLC, Mandeville, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/545,069

(22) Filed: Mar. 23, 2015

(65) Prior Publication Data

US 2015/0224051 A1 Aug. 13, 2015

Related U.S. Application Data

(60) Continuation-in-part of application No. 13/815,359, filed on Feb. 25, 2013, now Pat. No. 9,023,406, which is a continuation-in-part of application No. 13/029,551, filed on Feb. 17, 2011, now Pat. No. 8,399,032, which is a division of application No. 12/248,155, filed on Oct. 9, 2008, now abandoned, which is a continuation-in-part of application No. 11/441,878, filed on May 26, 2006, now abandoned.

(51) Int. Cl.

| *A61K 47/10* | (2006.01) |
|---|---|
| *A61K 47/14* | (2006.01) |
| *A61K 9/00* | (2006.01) |
| *A61K 47/44* | (2006.01) |
| *A61K 8/34* | (2006.01) |
| *A61K 8/37* | (2006.01) |
| *A61Q 19/02* | (2006.01) |
| *A61K 45/00* | (2006.01) |

(52) U.S. Cl.
CPC ............ *A61K 9/0014* (2013.01); *A61K 8/345* (2013.01); *A61K 8/375* (2013.01); *A61K 45/00* (2013.01); *A61K 47/10* (2013.01); *A61K 47/44* (2013.01); *A61Q 19/02* (2013.01)

(58) Field of Classification Search
CPC .... A61K 36/00; A61K 36/36; A61K 36/736; A61K 36/785; A61K 36/53
USPC .............................. 424/735, 745, 725, 78.03
See application file for complete search history.

(56) References Cited

U.S. PATENT DOCUMENTS

| 4,746,515 A | 5/1988 | Cheng et al. |
| 4,959,168 A * | 9/1990 | Schroeck ............. C07G 17/002 508/324 |
| 6,207,193 B1 | 3/2001 | Pellegrini et al. |
| 6,818,226 B2 | 11/2004 | Reed et al. |

* cited by examiner

*Primary Examiner* — Chris R Tate
*Assistant Examiner* — Deborah Davis

(57) ABSTRACT

The present invention is directed to compositions and processes for their use that allow for the delivery of physiologically active agents, using a unique composition containing glycerin and triglycerides in the proper ratio. The composition functions by acting both as a humectant and occlusive agent attracting water, returning the skin surface to a smooth state and holding water and physiologically active agents in place. The presence of both hydrophobic and hydrophilic components of the current invention solubilize the physiologically actives into the complex matrix, keeping the actives on the skin and allowing them to penetrate the skin over time, thus delivering the actives to the blood stream.

11 Claims, No Drawings

COMPOSITIONS FOR THE TRANSDERMAL DELIVERY OF PHYSIOLOGICALLY ACTIVE AGENTS

RELATED APPLICATIONS

The present invention is a continuation in part of co-pending U.S. Ser. No. 13/815,359 filed Feb. 25, 2013, which in turn is a continuation in part of U.S. Ser. No. 13/029,551 filed on Feb. 17, 2011 which is in turn a divisional application of U.S. Ser. No. 12/248,155, filed Oct. 9, 2008, and titled, "Bruise Amelioration Composition and Method of Use," which is in turn a continuation in part of U.S. Ser. No. 11/441,878, filed May 26, 2006, and titled, "Bruise Amelioration Composition and Method of Use." All of which are expressly incorporated by reference into the present application.

FIELD OF THE INVENTION

The present invention is directed to compositions and processes for their use that allow for the delivery of physiologically active agents, using a unique composition containing glycerin and triglycerides in the proper ratio. The composition functions by acting both as a humectant and occlusive agent attracting water, returning the skin surface to a smooth state and holding water and the physiologically active agents in place. The presence of both hydrophobic and hydrophilic components of the current invention solubilize the physiologically actives into the complex matrix, keeping the actives on the skin and allowing them to penetrate the skin over time, thus delivering the actives to the blood stream.

The ability to make a composition that contains glycerin, a humectant, and a triglyceride with a specified iodine value (which is a measure of unsaturation), provides a unique, heretofore-unappreciated composition that has stability and provides composition functions by acting both as a humectant and occlusive agent attracting water, returning the skin surface to a smooth state and holding water and the physiologically active agents in place.

BACKGROUND OF THE INVENTION

For some years, pharmaceutical researchers have sought an effective means of introducing drugs into the bloodstream by applying them to unbroken skin. Among other advantages, such administration can provide a comfortable, convenient, and safe way of giving many drugs now taken orally or infused into veins or injected intramuscularly.

Using skin as the portal for drug entry offers unique potential because transdermal delivery permits close control over drug absorption. For example, it avoids factors that can cause unpredictable absorption from the gastrointestinal tract, including: changes in acidity, motility, and food content. It avoids unpredictable drug absorption caused by inability to retain the drug for an adequate amount of time due to emesis. Thus, controlled drug entry through skin can achieve a high degree of control over blood concentrations of drug.

Close control over drug concentrations in blood can translate readily into safer and more comfortable and effective treatment. When a drug's adverse effects occur at higher concentrations than its beneficial ones, rate control can maintain the concentrations that evoke only—or principally the drug's desired actions. This ability to lessen undesired drug actions can greatly reduce the toxicity hazards that now restrict or prevent the use of many valuable agents.

Transdermal delivery particularly benefits patients with chronic disease and patients that are physically or mentally incapacitated. Many such patients have difficulty following regimens requiring several doses daily of medications that repeatedly cause unpleasant symptoms. They find the same drugs much more acceptable when administered in transdermal systems that require application infrequently—in some cases, only once or twice weekly—and that reduce adverse effects.

Transdermal delivery is feasible for drugs effective in amounts that can pass through the skin area and that are substantially free of localized irritating or allergic effects. While these limitations may exclude some agents, many others remain eligible for transdermal delivery. Moreover, their numbers will expand as pharmaceutical agents of greater potency are developed. Particularly suitable for transdermal delivery are potent drugs with only a narrow spread between their toxic and safe blood concentrations, those having gastrointestinal absorption problems, or those requiring frequent dosing in oral or injectable form.

Transdermal therapy permits much wider use of natural substances such as hormones. Often the survival times of these substances in the body are so short that they would have to be taken many times daily in ordinary dosage forms. Continuous transdermal delivery provides a practical way of giving them, and one that can mimic the body's own patterns of secretion.

The drug delivery system of the invention contributes significantly to the accelerated permeation of the drug through the skin, since the skin is continuously in contact with the drug in solution. Further, since the skin is occluded to permit hydration of water from the lower layers, the permeation of the drug from the liquid base material into the hydrated stratum corneum is much faster than when a dry, dehydrated corneum is presented. In addition, the skin is continuously in contact with the viscous liquid base material which is generally selected to have emollient properties. This emollient contributes to the accelerated delivery by maintaining the outer skin softness and pliability to assure continuous contact between the skin, the liquid base material and the membrane.

Since the early 1970s the main focus of transdermal systemic drug delivery has been, and still is, on transdermal patch devices. These patch devices are like bandages which are attached to the surface of intact skin for prolonged periods of time to allow a desired systemic delivery of a drug or other physiologically active agent. These transdermal patch devices occlude the skin and trap the drug, together with volatiles and vehicle excipients, between the skin and an outer impermeable backing membrane. The membrane prevents the evaporation or diffusion of vehicle excipients, volatiles and drug into an environment other than the target skin site. The prolonged length of time required for transfer of the drug and excipients from the patch into the skin can and often does result in local skin irritation. The irritation is caused by prolonged contact on the skin by the drug, volatiles, vehicle excipients, or the adhesive used to attach the patch device to the skin. The occlusive nature of the patch device also restricts the natural ability of the skin to "breathe", increasing the risk of irritation. With added problems of complex and costly manufacturing processes for transdermal patch devices there is a need for improved transdermal drug delivery systems.

The ability to hold physiologically active agents on the skin, both hydrophic types (oil soluble actives) and hydrophilic types (water soluble actives), allows for penetration of the actives into the skin. This delivery from a topical composition rather than a solid patch is a highly prized material in the drug delivery world. We have now surprisingly and unexpectantly found that the composition of the invention will solubilize a wide range of physiologically active agents and hold them on the skin.

Physiologically active agents that may be used in the transdermal drug delivery system of the present invention include any locally applied active agents which are compatible with the composition of the present invention and which can be delivered through the skin with the assistance of the composition to achieve a desired effect. These active agents (grouped by therapeutic class) include:

Alimentary System

Antidiarrheals such as diphenoxylate, loperamide and hyoscyamine.

Cardiovascular System

Antihypertensives such as hydralazine, minoxidil, captopril, enalapril, clonidine, prazosin, debrisoquine, diazoxide, guanethidne, methyldopa, reserpine, trimetaphan.

Calcium channel blockers such as diltiazem, felodopine, amlodipine, nitrendipine, nifedipine and verapamil.

Antiarrhythmics such as amiodarone, flecainide, disopyramide, procainamide, mexiletene and quinidine.

Antiangina agents such as glyceryl trinitrate, erythritol tetranitrate, pentaerythritol tetranitrate, mannitol hexanitrate, perhexilene, isosorbide dinitrate and nicorandil. Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate.

Cardiotonic glycosides such as digoxin and other cardiac glycosides and theophylline derivatives.

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine.

Vasodilators such as cyclandelate, isoxsuprine, papaverine, dipyrimadole, isosorbide dinitrate, phentolamine, nicotinyl alcohol, co-dergocrine, nicotinic acid, glyceryl trinitrate, pentaerythritol tetranitrate and xanthinol.

Antimigraine preparations such as ergotamine, dihydro-ergotamine, methysergide, pizotifen and sumatriptan.

Drugs Affecting Blood and Hemopoietic Tissues

Anticoagulants and thrombolytic agents such as warfarin, dicoumarol, low molecular weight heparins such as enoxaparin; streptokinase and its active derivatives. Hemostatic agents such as aprotinin, tranexamic acid and protamine.

Central Nervous System

Analgesics, antipyretics including the opiod analgesics-such as buprenorphine, dextromoramide, dextropropoxyphene, fentanyl, alfentanil, sufentanil, hydromorphone, methadone, morphine, oxycodone, papaveretum, pentazocine, pethidine, phenoperidine, codeine and dihydrocodeine. Others include acetylsalicylic acid (aspirin), paracetamol, and phenazone.

Hypnotics and sedatives such as the barbiturates, amylobarbitone, butobarbitone and pentobarbitone and other hypnotics and sedatives such as choral hydrate, chlormethiazole, hydroxyzine and meprobamate.

Antianxiety agents such as the benzodiazepines, alprazolam, bromazepam, chlordiazepoxide, clobazam, chlorazepate, diazepam, flunitrazepam, flurazepam, lorazepam, nitrazepam, oxazepam, temazepam and triazolam.

Neuroleptic and antipsychotic drugs such as the phenothiazines, chlorpromazine, fluphenazine, pericyazine, perphenazine, promazine, thiopropazate, thioridazine and trifluoperazine and the butyrophenones, droperidol and haloperidol and the other antipsychotic drugs such as pimozide, thiothixene and lithium.

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline.

CNS Stimulants Such as Caffeine.

Anti-alzheimer's agents such as tacrine.

Antiparkinson agents such as amantadine, benserazide, carbidopa, levodopa, benztropine, biperiden, benzhexol, procyclidine and dopamine-2 agonists such as S(-)-2-(N-propyl-N-2-thienylethylamino)-5-hydroxytetralin (N-0923).

Anticonvulsants such as phenytoin, valproic acid, primidone, phenobarbitone, methylphenobarbitone and carbamazepine, ethosuximide, methsuximide, phensuximide, sulthiame and clonazepam.

Antiemetics, antinauseants such as the phenothiazines, prochloperazine, thiethylperazine and 5HT-3 receptor antagonists such as ondansetron and granisetron and others such as dimenhydrinate, diphenhydramine, metoclopramide, domperidone, hyoscine, hyoscine hydrobromide, hyoscine hydrochloride, clebopride and brompride.

Musculoskeletal System

Non-steroidal anti-inflammatory agents including their racemic mixtures or individual enantiomers where applicable, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketoralac.

Additional non-steroidal antiinflammatory agents which can be formulated in combination with the dermal penetration enhancers include salicylamide, salicylic acid, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloide, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

Antirheumatoid agents such as penicillamine, aurothioglucose, sodium aurothiomalate, methotrexate and auranofin.

Muscle relaxants such as baclofen, diazepam, cyclobenzaprine hydrochloride, dantrolene, methocarbamol, orphenadrine and quinine.

Agents used in gout and hyperuricaemia such as allopurinol, colchicine, probenecid and sulphinpyrazone.

Hormones and Steroids

Estrogens such as estradiol, estriol, estrone, ethinyloestradiol, mestranol, stilboestrol, dienestrol, epiestriol, estropipate and zeranol.

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol.

Antiandrogens such as cyproterone acetate and danazol.

Antiestrogens such as tamoxifen and epitiostanol and the aromatase inhibitors, exemestane and 4-hydroxy-androstenedione and its derivatives.

Androgens and anabolic agents such as testosterone, methyltestosterone, clostebol acetate, drostanolone, furazabol, nandrolone oxandrolone, stanozolol, trenbolone acetate, dihydro-testosterone, 17-.alpha.-methyl-19-nortestosterone and fluoxymesterone.

5-alpha reductase inhibitors such as finasteride, turosteride, LY-191704 and MK-306.

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate methylprednisolone, prednisolone, prednisolone 21-phosphate, prednisone, triamcinolone, triamcinolone acetonide.

Further examples of steroidal antiinflammatory agents for use in the instant compositions include include cortodoxone, fluoracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol.

Pituitary hormones and their active derivatives or analogs such as corticotrophin, thyrotropin, follicle stimulating hormone (FSH), luteinising hormone (LH) and gonadotrophin releasing hormone (GnRH).

Hypoglycaemic agents such as insulin, chlorpropamide, glibenclamide, gliclazide, glipizide, tolazamide, tolbutamide and metformin.

Thyroid hormones such as calcitonin, thyroxine and liothyronine and antithyroid agents such as carbimazole and propylthiouracil.

Other miscellaneous hormone agents such as octreotide.

Pituitary inhibitors such as bromocriptine.

Ovulation inducers such as clomiphene.

Genitourinary System

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and pottasium sparing diuretics, spironolactone, amiloride and triamterene.

Antidiuretics such as desmopressin, lypressin and vasopressin including their active derivatives or analogs.

Obstetric drugs including agents acting on the uterus such as ergometrine, oxytocin and gemeprost.

Prostaglandins such as alprostadil (PGE1), prostacyclin (PGI2), dinoprost (prostaglandin F2-alpha) and misoprostol.

Antimicrobials

Antimicrobials including the cephalosporins such as cephalexin, cefoxytin and cephalothin.

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, mezlocillin, piperacillin, ticarcillin and azlocillin.

Tetracyclines such as minocycline, chlortetracycline, tetracycline, demeclocycline, doxycycline, methacycline and oxytetracycline and other tetracycline-type antibiotics. Aminoglycosides such as amikacin, gentamicin, kanamycin, neomycin, netilmicin and tobramycin.

Antifungais such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione.

Quinolones such as nalidixic acid, cinoxacin, ciprofloxacin, enoxacin and norfloxacin. Sulphonamides such as phthalylsulphthiazole, sulfadoxine, sulphadiazine, sulphamethizole and sulphamethoxazole.

Sulphones such as dapsone.

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonam, colistin IV, metronidazole, tinidazole, fusidic acid and trimethoprim; 2-thiopyridine N-oxide; halogen compounds, particularly iodine and iodine compounds such as iodine-PVP complex and diiodohydroxyquin; hexachlorophene; chlorhexidine; chloroamine compounds; benzoylperoxide.

Antituberculosis drugs such as ethambutol, isoniazid, pyrazinamide, rifampicin and clofazimine.

Antimalarials such as primaquine, pyrimethamine, chloroquine, hydroxychloroquine, quinine, mefloquine and halofantrine.

Antiviral agents such as acyclovir and acyclovir prodrugs, famciclovir, zidovudine, didanosine, stavudine, lamivudine, zalcitabine, saquinavir, indinavir, ritonavir, n-docosanol, tromantadine and idoxuridine.

Anthelmintics such as mebendazole, thiabendazole, niclosamide, praziquantel, pyrantel embonate and diethylcarbamazine.

Cytotoxic agents such as plicamycin, cyclophosphamide, dacarbazine, fluorouracil and its prodrugs, methotrexate, procarbazine, 6-mercaptopurine and mucophenolic acid.

Metabolism

Anorectic and weight reducing agents including dexfenfluramine, fenfluramine, diethylpropion, mazindol and phentermine.

Agents used in hypercalcaemia such as calcitriol, dihydrotachysterol and their active derivatives or analogs.

Respiratory System

Antitussives such as ethylmorphine, dextromethorphan and pholcodine.

Expectorants such as acetylcysteine, bromhexine, emetine, guaiphenesin, ipecacuanha and saponins.

Decongestants such as phenylephrine, phenylpropanolamine and pseudoephedrine.

Bronchospasm relaxants such as ephedrine, fenoterol, orciprenaline, rimiterol, salbutamol, sodium cromoglycate, cromoglycic acid and its prodrugs, terbutaline, ipratropium bromide, salmeterol and theophylline and theophylline derivatives.

Allergy and Immune System

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine.

Local anaesthetics such as lidocaine, benzocaine, tetracaine, chloroprocaine, ropivacaine, bupivacaine, amethocaine, lignocaine, cinchocaine, dibucaine, mepivacaine, prilocaine and etidocaine.

Stratum corneum lipids, such as ceramides, cholesterol and free fatty acids, for improved skin barrier repair.

Neuromuscular blocking agents such as suxamethonium, alcuronium, pancuronium, atracurium, gallamine, tubocurarine and vecuronium.

Smoking cessation agents such as nicotine, bupropion and ibogaine.

Insecticides and other pesticides which are suitable for local or systemic application.

Dermatological agents, such as zinc, bioflavinoids, vitamin K-2, vitamin D, vitamin C, vitamin A, vitamin E, vitamin E acetate and vitamin E sorbate.

Allergens for desensitisation such as house dust mite allergen.

Nutritional agents, such as vitamins, essential amino acids and essential fats.

Keratolytics such as the alpha-hydroxy acids, glycollic acid and salicylic acid.

Psychicenergisers, such as 3-(2-aminopropyl)indole, 3-(2-aminobutyl)indole, and the like.

Anti-acne agents such as containing isotretinoin, tretinoin and benzoyl peroxide.

Anti-psoriasis agents such as containing etretinate, cyclosporin and calcipotriol.

Anti-itch agents such as capsaicin and its derivatives such as nonivamide.

Anticholinergic agents, which are effective for the inhibition of axillary sweating and for the control of prickly heat. The antiperspirrant activity of agents such as methatropine nitrate, propantheline bromide, scopolamine, methscopolamine bromide, and the new class of soft antiperspirants, quaternary acyloxymethyl ammonium salts.

Other physiologically active peptides and proteins, small to medium-sized peptides, e.g., vasopressin and human growth hormone.

The term "physiologically active agent" is used herein to refer to a broad class of useful chemical and therapeutic agents. The term "drug" is used herein to refer to physiologically active agents.

The term "physiologically active" in describing the agents contemplated herein is used in a broad sense to comprehend not only agents having a direct pharmalogical effect on the host, but also those having an indirect or observable effect which is useful in the medical arts.

The term "physiologically active amount" refers to the amount of an active ingredient, or combination of active ingredients, that will elicit the biological or medical response that is being sought by the researcher, veterinarian, medical doctor or other clinician. Alternatively, a therapeutically effective amount of an active ingredient is the quantity of the compound required to achieve a desired therapeutic and/or prophylactic effect, such as the amount of the active ingredient that results in the prevention of or a decrease in the symptoms associated with the condition (for example, to meet an end-point).

A "prodrug" of a physiologically active agent herein means a structurally related compound or derivative of an active compound which in the animal body is converted to the desired physiologically active compound. The prodrug itself may have little or none of the desired activity.

In addition physiologically active agent comprises one or more selected from the group consisting of: androgens, estrogens, selective estrogen receptor modulators, aromatase inhibitors, gonadotropins, progesterone, progestins, selective progesterone receptor modulators, antiprogestogen, antigonadotropins, GnRH:(receptor) agonists, antidiarrhoeals, cardiovascular system agents, antihypertensives, calcium channel blockers, proton pump inhibitors, antiarrhythmics, antiangina, beta-adrenergic blocking agents, cardiotonic glycosides, adrenergic stimulants, vasodilators, antimigraine preparations, anticoagulants, haemostatic agents, analgesics, antipyretics, hypnotics, antianxiety, neuroleptic and antipsychotic drugs, antidepressants, CNS stimulants such as caffeine, anti-alzheimer's agents, antiparkinson agents, lipid regulating drugs, anticonvulsants, antiemetics, antinauseants, non-steroidal antiinflammatory agents, antirheumatoid, muscle relaxants, agents used in gout and hyperuricaemia, diuretics, antidiuretics, obstetric drugs, prostaglandins, antimicrobials, antituberculosis drugs, antimalarials, antiviral agents, anthelmintics, cytotoxic agents, anorectics, agents used in hypercalcaemia, antitussives, expectorants, decongestants, bronchospasm relaxants, antihistamines, local anaesthetics, stratum corneum lipids, H2-receptor antagonists, neuromuscular blocking agents, smoking cessation agents, insecticides and other pesticides, dermatological agents, allergens, nutraceutically active compounds, keratolytics, psychicenergisers, anti-acne agents, anti-psoriasis agents, anti-itch agents, anticholinergic agents, and mixtures thereof.

It is to be understood that the above list of drugs is for purposes of illustration and is not provided as an all-inclusive list of all the drugs which may be beneficially formulated or reformulated using the compositions of the present invention.

According to our invention, we have discovered that our glycerin/triglyceride composition provides a unique medium for transport of a physiologically active agent across the dermis. Various other materials have been suggested for this purpose as described in U.S. Pat. Nos. 4,746,515, 6,818,226, and 6,207,193, all of which are incorporated herein by reference.

None of the art cited above, alone or in combination makes obvious or anticipates the current invention.

THE INVENTION

Object of the Invention

It is the object of the present invention to provide a composition that comprises a carefully selected level of glycerin and of triglyceride to provide a serum or gel that, when applied to skin, provides an occlusive barrier to the skin and a physiologically active agent. This composition can be absorbed into the skin in a stable thick dispersion.

Another object of the present invention is to provide a process for providing physiologically active agents to the skin. This is accomplished by applying to the skin the concentration of the composition of the present invention. Other objectives will become clear as one reads the specification.

All temperatures are degrees centigrade, and all percentages are percentage by weight.

SUMMARY OF THE INVENTION

The present invention is directed to a thick dispersion of glycerin and triglyceride wherein the concentration of glycerin ranges from 80 to 98% by weight and the concentration of triglyceride ranges from 1 to 19% by weight and a physiologically active agent from 1-5% by weight. The triglyceride must have an iodine value of between 100 and 160 mg KOH/gram to provide a stable dispersion.

This dispersion contains both a humectant (glycerin) and an occlusive agent (triglyceride) that functions to deliver physiologically active agents.

DETAILED DESCRIPTION OF THE INVENTION

A composition that comprises:
(a) between 80 and 98% by weight of glycerin, and
(b) between 1 and 15% of a triglyceride having an iodine value of between 100 and 160 mg KOH/gm, and
(c) a physiologically active agent from 1-5% by weight.

In a preferred embodiment, a composition that comprises:
(a) between 85 and 94% by weight of glycerin, and
(b) between 5 and 12% of a triglyceride having an iodine value of between 100 and 160 mg KOH/gm, and
(c) a physiologically active agent from 1-3% by weight.

In a more preferred embodiment, a composition that comprises:
(a) between 80 and 90% by weight of glycerin, and
(b) between 9 and 19% of a triglyceride having an iodine value of between 100 and 160 mg KOH/gm, and
(c) a physiologically active agent of 1% by weight.

A process for transdermal delivery of a physiologically active agent, which comprises contacting the skin with an effective physiologically active concentration of a composition, which comprises:
(a) between 80 and 98% by weight of glycerin, and
(b) between 1 and 15% of a triglyceride having an iodine value of between 100 and 160 mg KOH/gm, and
(c) a physiologically active agent from 1-5% by weight.

In a preferred embodiment the concentration of glycerin ranges from 85-94% by weight, the concentration of triglyceride ranges from 5-12% by weight, and the concentration of a physiologically active agent ranges from 1-3% by weight.

In a more preferred embodiment the concentration of glycerin ranges from 80-90% by weight, the concentration of triglyceride ranges from 9-19% by weight, and the concentration of a physiologically active agent ranges of 1% by weight.

EXAMPLES

Glycerin

Glycerin is an item of commerce. It conforms to the following structure:

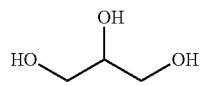

Glycerin has an IUPAC name of 1,2,3-triol and a CAS number of 56-81-5.

Iodine Value

We have surprisingly found that triglycerides with a specific level of unsaturation provide the stable dispersion we seek for the compositions of the present invention. Iodine value (IV) is a measure of the unsaturation present in particular chemical. The higher the iodine value, the more double bonds are in the molecule. The preferred method is known as the Wijs procedure, it is commonly used.

Iodine value is a measure of the total number of double bonds present in fats and oils. It is generally expressed in terms of "the number of grams of iodine that will react with the double bonds in 100 grams of fats or oils".

Oils with a high iodine value contain a greater number of double bonds than low iodine value oils. Edible oils with high IV are less stable and susceptible to oxidation.

The American Oil Chemists' Society (AOCS) recommends the use of ASTM method D1959-97, also known as the Wijs method, for determination of IV. The method involves the addition of Wijs solution to the sample, after which it is allowed to stand in the dark. The reaction is complete after approximately 30 min, at which time potassium iodide is added. The liberated iodine is then titrated with sodium thiosulfate, using a standard starch solution as the indicator.

EXAMPLES

Triglycerides

Natural oils chemically are triglycerides. Triglyceride is an ester derived from glycerol and three fatty acids conforming to the following structure:

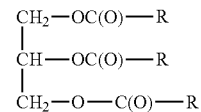

The triglycerides that are useful in making the compositions of the present invention R are over 50% by weight C18. The triglycerides are also unsaturated. The level of unsaturation is measured by iodine value that is expressed in mg KOH/gm.

We have found that the iodine value needed to make the compounds of the present invention needs to be over 100 mg KOH/gram and less than 160 mg KOH/gm. This is because this specific type of triglyceride, when blended with glycerin in the range of 1 to 20% by weight of the triglyceride, results in a thick stable dispersion. It is this thick dispersion that results in a truly multifunctional composition.

While not wanting to be bound by a particular theory, the applicants believe that the iodine value of these triglycerides, which is an indication of the double bonds present in the oil when properly selected, allows for stable dispersions of the triglyceride in the glycerin. Additionally and very importantly, the presence of the triglyceride in the glycerin over the specifically specified range results in a composition that provides both humectant properties and minimized transepidermal water loss (occlusive properties), both of which aid in transdermal drug delivery of physiologically active agents. It is the critical combination of (a) the concentration of the glycerin relative to the triglyceride, and (b) the amount of unsaturation of the triglyceride as measured by iodine value, that provides the unique properties required to deliver physiologically active agents transdermally.

The triglycerides useful in the preparation of the compositions of the present invention, Examples 1-15, are natural products and are listed in the below table. Example 16 in this table is not a triglyceride useful in the preparation of the composition of the present invention but is included as it is referenced in Examples include herein.

| Example | Product | Genus/species | Iodine Value (KOH/gm) |
|---|---|---|---|
| 1 | Sunflower Seed Oil | Helianthus annuus | 130 |
| 2 | Apricot Kernel Oil | Prunus armeniaca | 102 |
| 3 | Argan Oil | Argania spinosa | 100 |
| 4 | Cottonseed Oil | Gossypium hirsutum | 108 |
| 5 | Rice Bran Oil | Oryza sativa | 105 |
| 6 | Wheat germ Oil | Triticum vulgare | 130 |
| 7 | Vernonia Oil | Vernonia galamensis | 106 |
| 8 | Poppy Seed Oil | Populus nigra | 138 |
| 9 | Grape Seed Oil | Vitis vinifera | 135 |
| 10 | Sesame Oil | Sesamum indicum | 110 |
| 11 | Sweet Almond Oil | Prunus amygdalus dulcis | 102 |
| 12 | Soybean Oil | Glycine soja | 130 |
| 13 | Safflower Oil | Carthamus tinctorius | 145 |
| 14 | Walnut Oil | Juglans regia | 150 |
| 15 | Evening Primrose Oil | Denothera biennis | 152 |
| 16 | Olive Oil | Olea eruopaea | 84 |

In order to demonstrate the effectiveness of the compositions of the present invention, several dispersions were made using a variety of triglycerides.

General Procedure

The specified number of grams of the specified triglyceride (example 1-16) was added to glycerin under agitation over a range of concentrations, under good agitation. The material was mixed for about 30 minutes, whereupon it was passed through a Silverson homogenizer. After 30 minutes at room temperature the product was evaluated for the presence of a separation into an oil and water phase.

Example 17

| Material | % wt | Grams |
|---|---|---|
| Glycerin | 97.0 | 970.0 |
| Example 15 | 2.0 | 20.0 |
| Physiologically active agent | 1.0 | 10.0 |

A translucent thick dispersion was obtained that was stable overnight.

Example 18

| Material | % wt | Grams |
|---|---|---|
| Glycerin | 90.0 | 900.0 |
| Example 15 | 9.0 | 90.0 |
| Physiologically active agent | 1.0 | 10.0 |

A less translucent uniform thick dispersion was obtained that was stable overnight.

Example 19

| Material | % wt | Grams |
|---|---|---|
| Glycerin | 80.0 | 800.0 |
| Example 15 | 19.0 | 190.0 |
| Physiologically Active Agent | 1.0 | 10.0 |

An opaque thick dispersion was obtained that was stable overnight.

Example 20

Control Example—not of the Present Invention

| Material | % wt | Grams |
|---|---|---|
| Glycerin | 69.0 | 690.0 |
| Example 15 | 30.0 | 300.0 |
| Physiologically active agent | 1.0 | 10.0 |

Nonstable products that split into two layers was observed.

Hydrophobicity

Despite the fact that the formulation was predominantly glycerin (water soluble), the compositions rendered a glass substrate hydrophobic, indicating we have indeed discovered a way to keep hydrophilic humectants (glycerin) on the skin in a hydrophobic formulation, thus providing both moisturization by humectancy and by occlusive mechanisms.

Examples 17-20 were evaluated using a microscope slide dip process (MSDP). In this test a 200 grams of the composition are placed into a 400 ml beaker and microscope slide is dipped into the composition and allowed to remain 5 minutes at room temperature, whereupon the appearance of the slide is evaluated. The slide is removed and left exposed to the air for 5 minutes. A drop of water is then added and the slide is evaluated as the $2^{nd}$ evaluation.

$1^{st}$ Evaluation Scoring System

| 0 | No coating |
|---|---|
| 1 | Little coating |
| 2 | Some coating |
| 3 | Uniform coating (thin) |
| 4 | Uniform coating (intermediate) |
| 5 | Thick uniform coating |

$2^{nd}$ Evaluation Scoring System

| 0 | No effect |
|---|---|
| 1 | Water runs off |
| 2 | Minimal drop formation |
| 3 | Flat water droplets (small) |
| 4 | Flat water droplets (medium) |
| 5 | Stable water droplet on surface |

Evaluation of MSDP Results

| Example | $1^{st}$ Evaluation | $2^{nd}$ Evaluation |
|---|---|---|
| 17 | 3 | 4 |
| 18 | 4 | 5 |
| 19 | 5 | 4 |

-continued

| Example | 1st Evaluation | 2nd Evaluation |
| --- | --- | --- |
| 20 | 0 | 0 |
| Glycerin alone | 0 | 0 |

The composition with 90% glycerin by weight is tenacious to water and hydrophobic, providing the two types of moisturization mechanisms, occlusive film minimizing transepidermal water loss and humectancy attracting and retaining water.

Human Forearm Test (HFT)

The following process was performed on human forearms for Examples 17-20 using the following procedure:
0.5 ml of compositions was applied to the forearm and rubbed on the skin of the forearm to an area the size of a quarter. After 5 minutes a drop of water was applied.

Evaluation of HFT Results

| Example | 1st Evaluation | 2nd Evaluation |
| --- | --- | --- |
| 17 | 4 | 4 |
| 18 | 4 | 4 |
| 19 | 4 | 4 |
| 20 | 0 | 0 |
| Glycerin alone | 0 | 0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove, but rather that the claims be construed as encompassing all the features of patentable novelty which reside in the present invention, including all features which would be treated as equivalents thereof by those skilled in the art to which the invention pertains.

The invention claimed is:

1. A topical composition for the transdermal delivery of a physiological active agent that comprises:
 (a) between 80 and 98% by weight of glycerin, and
 (b) between 1 and 15% by weight of a triglyceride having an iodine value of between 100 and 160 mg KOH/gm; and
 (c) between 1 and 5% by weight of the physiologically active agent.

2. The composition of claim 1 wherein the concentration of said glycerin ranges from 85-94% by weight, the concentration of said triglyceride ranges from 5-12% by weight, and the concentration of said physiologically active agent ranges from 1-3% by weight.

3. The topical composition of claim 1 wherein the concentration of said glycerin ranges from 80-90% by weight, the concentration of said triglyceride ranges from 9-15% by weight, and the concentration of said physiologically active agent of 1% by weight.

4. The topical composition of claim 1 wherein the iodine value of said triglyceride ranges from between 105 and 140 mg KOH/gm.

5. The topical composition of claim 1 wherein the iodine value of said triglyceride ranges from between 125 and 155 mg KOH/gm.

6. A process for the transdermal delivery of a physiologically active agent, which comprises contacting the skin of a subject with an effective amount of a topical composition that comprises:
 (a) between 80 and 98% by weight of glycerin, and
 (b) between 1 and 15% of a triglyceride having an iodine value of between 100 and 160 mg KOH/gm, and
 (c) between 1 and 5% by weight of said physiologically active agent.

7. The process of claim 6 wherein the concentration of said glycerin ranges from 85-94% by weight, the concentration of said triglyceride ranges from 5-12% by weight, and the concentration of said physiologically active agent ranges from 1-3% by weight.

8. The process of claim 6 wherein the concentration of said glycerin ranges from 80-90% by weight, the concentration of said triglyceride ranges from 9-15% by weight, and the concentration of said physiologically active agent of 1% by weight.

9. The process of claim 6 wherein the iodine value of said triglyceride ranges from between 105 and 140 mg KOH/gm.

10. The process of claim 6 wherein the iodine value of said triglyceride ranges from between 125 and 155 mg KOH/gm.

11. The process of claim 6 wherein the composition further comprises one or more additives selected from the group consisting of Vitamin E, Vitamin C, Vitamin D, retinol, flavonoids, antioxidants, anti-acne including azelic acid, alpha hydroxy acids including glycolic acid, beta hydroxy acids including salicylic acid.

* * * * *